(12) United States Patent
Stoddard et al.

(10) Patent No.: US 9,655,641 B2
(45) Date of Patent: May 23, 2017

(54) ULTRASONIC SURGICAL INSTRUMENT WITH COOLING SYSTEM

(71) Applicant: COVIDIEN LP, Mansfield, MA (US)

(72) Inventors: Robert B. Stoddard, Steamboat Springs, CO (US); Eric R. Larson, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 260 days.

(21) Appl. No.: 14/284,888

(22) Filed: May 22, 2014

(65) Prior Publication Data
US 2015/0073458 A1 Mar. 12, 2015

Related U.S. Application Data

(60) Provisional application No. 61/876,457, filed on Sep. 11, 2013, provisional application No. 61/876,449, filed on Sep. 11, 2013.

(51) Int. Cl.
*A61B 17/32* (2006.01)
*A61B 17/00* (2006.01)

(52) U.S. Cl.
CPC ............. *A61B 17/320068* (2013.01); *A61B 2017/00017* (2013.01); *A61B 2017/320084* (2013.01)

(58) Field of Classification Search
CPC .. A61B 17/320068; A61B 2017/00017; A61B 2017/320084
See application file for complete search history.

(56) References Cited

U.S. PATENT DOCUMENTS

| 4,681,561 | A | 7/1987 | Hood et al. |
| 4,724,834 | A | 2/1988 | Alperovich et al. |
| 5,383,876 | A | 1/1995 | Nardella |
| 5,391,144 | A | 2/1995 | Sakurai et al. |
| 6,206,876 | B1 | 3/2001 | Levine et al. |
| 6,379,371 | B1 * | 4/2002 | Novak ............... A61F 9/00754 30/301 |
| 6,764,487 | B2 | 7/2004 | Mulier et al. |
| 7,074,219 | B2 | 7/2006 | Levine et al. |
| 8,348,880 | B2 | 1/2013 | Messerly et al. |
| 2002/0091404 | A1 | 7/2002 | Beaupre |
| 2003/0181904 | A1 | 9/2003 | Levine et al. |
| 2003/0204199 | A1 | 10/2003 | Novak et al. |
| 2005/0209578 | A1 | 9/2005 | Christian Evans et al. |
| 2007/0233054 | A1 | 10/2007 | Babaev |
| 2008/0015563 | A1 | 1/2008 | Hoey et al. |

(Continued)

FOREIGN PATENT DOCUMENTS

| CN | 201939898 U | 8/2011 |
| EP | 00514810 A1 | 11/1992 |

(Continued)

OTHER PUBLICATIONS

European Search Report dated Dec. 12, 2014 issued in EP 14 18 4056.

(Continued)

*Primary Examiner* — Gregory Anderson

(57) ABSTRACT

A method of treating tissue includes ultrasonically treating tissue by oscillating a blade of an ultrasonic surgical instrument in contact with tissue and activating a fluid control system to pump cooling fluid through a blade conduit of the blade to cool the blade.

7 Claims, 8 Drawing Sheets

(56) References Cited

U.S. PATENT DOCUMENTS

| | | |
|---|---|---|
| 2009/0036914 A1 | 2/2009 | Houser |
| 2012/0253371 A1 | 10/2012 | Ross et al. |
| 2013/0072950 A1 | 3/2013 | Ross et al. |
| 2013/0178842 A1 | 7/2013 | Reid, Jr. |
| 2014/0276369 A1 | 9/2014 | Banko |

FOREIGN PATENT DOCUMENTS

| | | |
|---|---|---|
| EP | 2572660 A2 | 3/2013 |
| JP | S1020543 A | 8/1987 |
| JP | 01151452 A | 6/1989 |
| JP | 2005160735 A | 6/2005 |
| JP | 04089043 B2 | 5/2008 |
| JP | 2014000311 A | 1/2014 |
| JP | 2014233540 A | 12/2014 |
| WO | 2009032438 A2 | 3/2009 |
| WO | 2014196226 A1 | 12/2014 |

OTHER PUBLICATIONS

U.S. Appl. No. 14/284,741, filed May 22, 2014 (Stoddard).
European Search Report dated Jul. 14, 2016, issued in EP Application No. 15191718.
Japanese Office Action dated Jul. 26, 2016, issued in JP Application No. 2015-211714.
Australian Examination Report dated Jun. 17, 2016, issued in Australian Application No. 2015249032.
Australian Examination Report dated Dec. 22, 2016, issued in Australian Application No. 2015249032.
Japanese Office Action dated Feb. 8, 2017, issued in Japanese Application No. 2015-211714.

\* cited by examiner

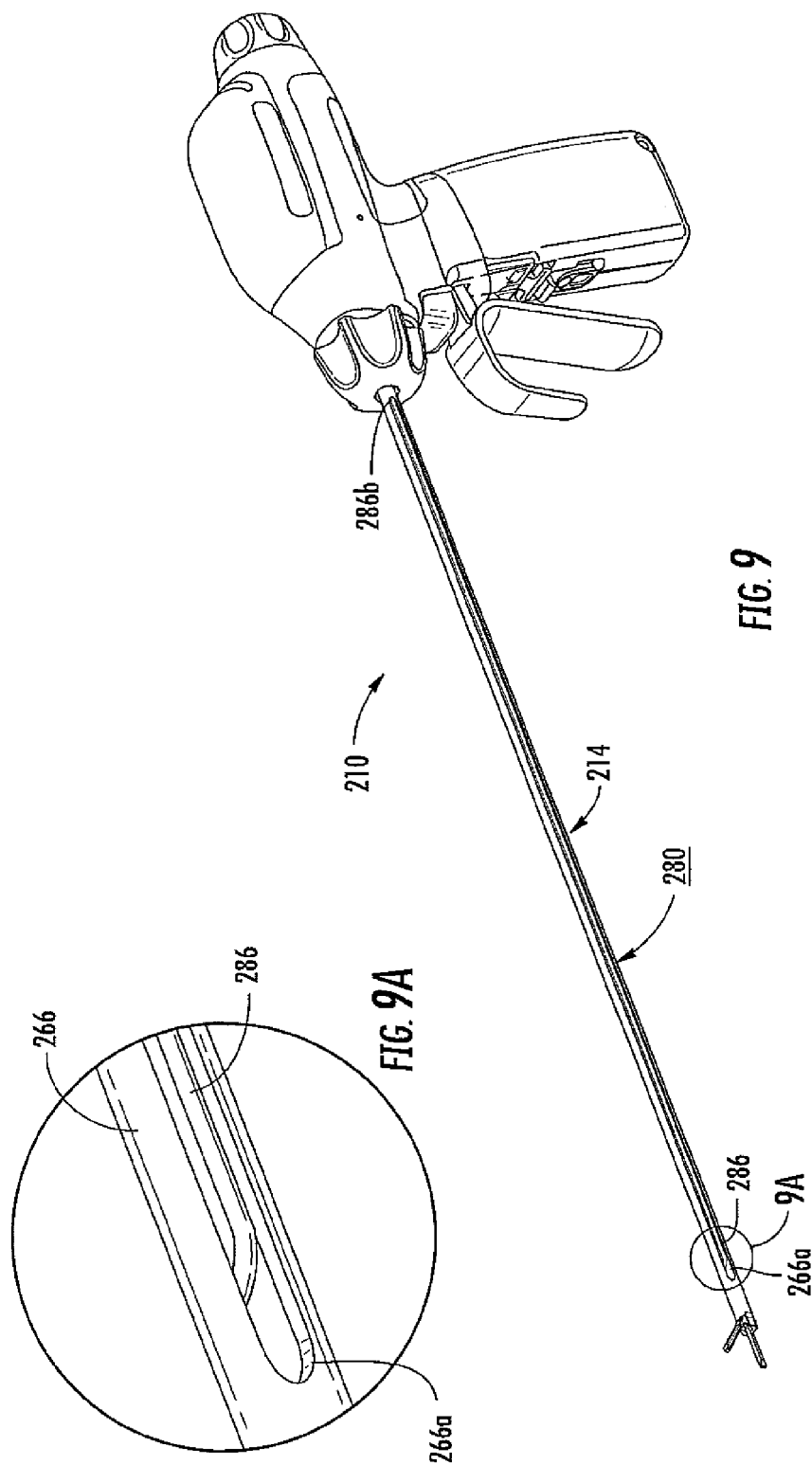

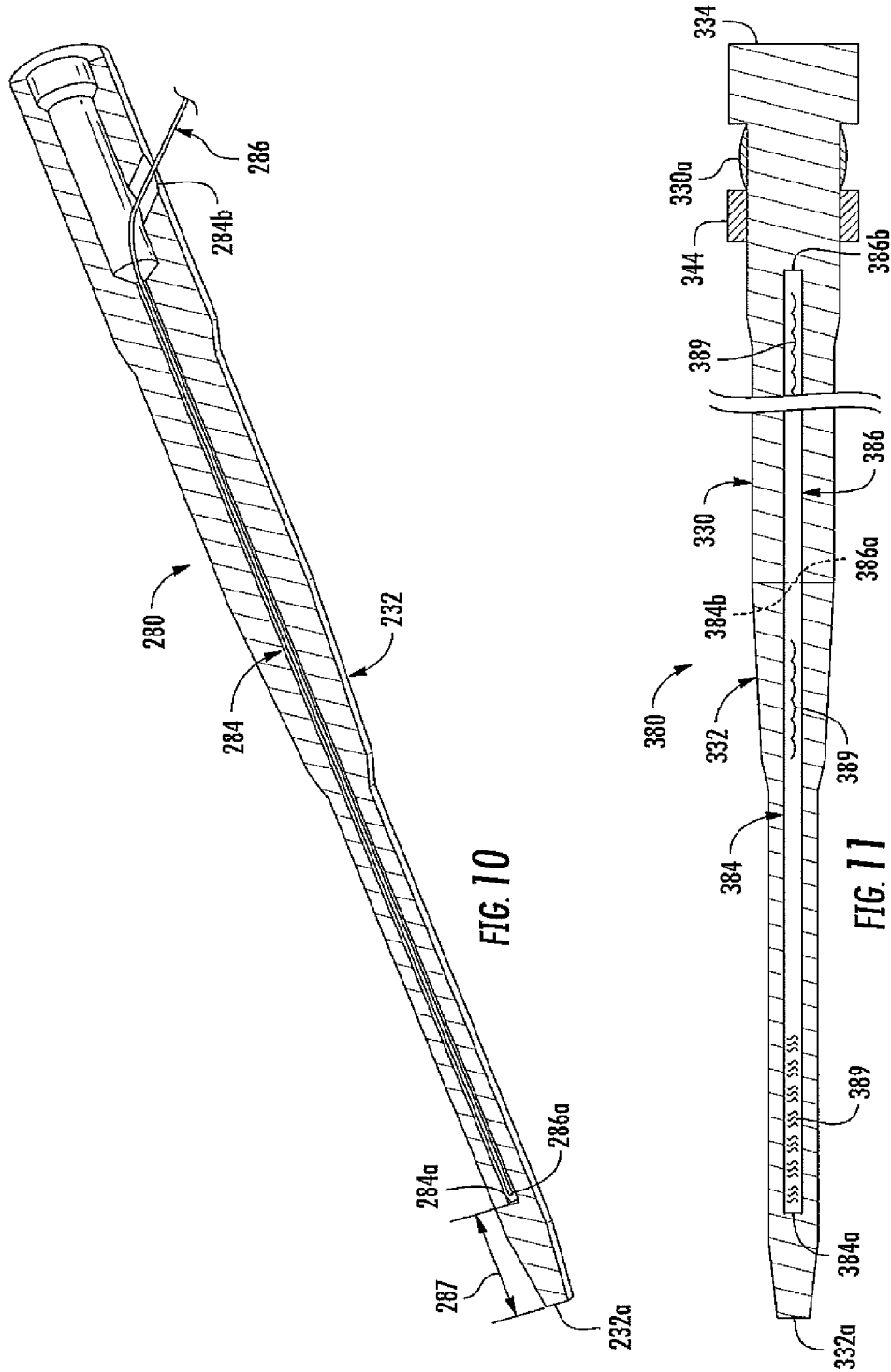

ULTRASONIC SURGICAL INSTRUMENT WITH COOLING SYSTEM

CROSS-REFERENCE TO RELATED APPLICATIONS

This application claims the benefit of and priority to U.S. Provisional Patent Application Nos. 61/876,449 and 61/876,457, both of which were filed on Sep. 11, 2013. This application is related to U.S. patent application Ser. No. 14/284,741, filed on May 22, 2014. The entire contents of each of the above applications are incorporated herein by reference.

BACKGROUND

1. Technical Field

The present disclosure relates generally to surgical instruments, and in particular, to ultrasonic surgical instruments having fluid-cooled components and related methods of cooling ultrasonic surgical instruments.

2. Discussion of Related Art

Energy-based tissue treatment is well known in the art. Various types of energy (e.g., electrical, ultrasonic, microwave, cryogenic, thermal, laser, etc.) are applied to tissue to achieve a desired result. Ultrasonic energy, for example, may be delivered to tissue using a surgical probe that includes a transducer coupled with an end effector configured to deliver the ultrasonic energy to tissue.

A typical ultrasonic surgical instrument incorporates a sinusoidal driving signal which causes the mechanical tip of a waveguide to vibrate at a selected frequency, usually in the range of 20 KHz to 60 KHz, for cutting and/or coagulating tissue. Improved cutting may result from increased tissue-to-mechanical tip coupling caused by the high frequency of vibration of the mechanical tip in relation to tissue. Improved coagulation may result from heat generated by coupling between the high frequency vibrations of the mechanical tip and body tissue.

Ultrasonic surgical instruments may include any of a variety of waveguides configured to achieve a surgical result. For example, an ultrasonic waveguide may be disposed at a distal end of the ultrasonic instrument. The waveguide may include an end effector that includes a cutting blade, shears, a hook, a ball, etc., and may be combined with other features such as jaws for grasping or manipulating tissue. During use, waveguides on ultrasonic surgical instruments can reach temperatures greater than 200° C.

SUMMARY

According to an aspect of the present disclosure, an ultrasonic surgical instrument includes a handle assembly, an elongated body member, a tool assembly, and a blade cooling system. The elongated body member extends distally from the handle assembly and defines a longitudinal axis. The elongated body member includes a waveguide positioned coaxially within a lumen of an outer tube. The tool assembly is coupled to a distal end of the elongated body member and includes a blade coupled to the distal end of the wave guide. The blade configured to oscillate with respect to the outer tube for ultrasonically treating tissue. The blade cooling system includes a blade conduit extending at least partially through the blade. A cooling fluid is configured to flow through the blade conduit. In embodiments, the blade cooling system is a closed-loop system. In some embodiments, the blade cooling system is an open system.

The elongated body member can also include a cooling conduit in fluid communication with the blade conduit. In aspects, the cooling conduit is defined between the outer tube and the waveguide. In particular aspects, the cooling conduit is constructed of a microtube. In certain aspects, the cooling conduit and the blade conduit form a fully enclosed heat pipe such that the cooling fluid is configured to absorb heat from the blade and the cooling conduit is configured to release the absorbed heat to the surrounding environment.

In aspects, the blade conduit includes a blade outlet in a distal surface of the blade. The blade cooling system may also include an inflow conduit in fluid communication with the blade conduit. In some aspects, the inflow conduit is constructed of a microtube. In particular aspects, the blade cooling system further includes a return conduit in fluid communication with the blade conduit. The return conduit can also be constructed of a polyimide microtube. In certain embodiments, the blade conduit includes a blade inlet between the inflow conduit and the blade conduit and positioned in a proximal portion of the blade. The blade conduit can extend distally within the blade in parallel orientation relative to the longitudinal axis to a first end of a distal section of the blade conduit which is orthogonal to the longitudinal axis and spaced apart from a distal surface of the blade. A second segment of the blade conduit extends proximally within the blade in parallel orientation to the longitudinal axis from a second end of the distal segment to a blade outlet. The blade conduit forms a continuous flow path through the blade from the blade inlet through the distal section and exiting through the blade outlet. The blade outlet can be distal to the blade inlet. The distal section of the blade conduit is spaced-apart from the distal surface of the blade a distance in the range of 0.005 to 0.025 mm.

According to another aspect of the present disclosure a surgical system includes an ultrasonic instrument and a blade cooling system. The ultrasonic instrument includes a handle assembly, an elongated body member, and a tool assembly. The elongated body member includes a waveguide having a blade coupled to the distal end. The blade configured to oscillate with respect to the outer tube to ultrasonically treat tissue. The blade cooling system includes a blade conduit, an inflow conduit, and a fluid control system. The blade conduit is disposed within and along the length of the blade. The inflow conduit is disposed within and along the length of the elongated body member. The fluid control system includes a pump configured to pump cooling fluid through the inflow conduit and the blade conduit.

The blade cooling system can also include a fluid reservoir storing a cooling fluid therein such that the pump is configured to draw the cooling fluid from the fluid reservoir. In aspects, the blade cooling system further includes a return conduit and the blade conduit includes a distal section orthogonal to the longitudinal axis of the blade. The distal section spaced-apart from a distal surface of the blade. The fluid control system configured to pump the cooling fluid through the inflow conduit, through the blade conduit including the distal section, and through the return conduit. The return conduit in fluid communication with the inflow conduit such that the blade cooling system is a closed-loop system.

In aspects, the fluid control system controls activation and deactivation of the pump in accordance with at least one property or condition of the ultrasonic instrument. More specifically, a first sensor may be provided to sense a temperature of the blade. The fluid control system may thus be configured to activate the pump when the temperature of the blade exceeds an upper temperature limit and/or deactivate the pump when the temperature of the blade is less than a lower temperature limit. A second sensor configured to sense a position of an activation button of the ultrasonic instrument may additionally or alternatively be provided. The fluid control system may thus be configured to activate and deactivate the pump for predetermined periods of time according to the position of the activation button (independently of or in conjunction with temperature-based feedback control).

According to another aspect of the present disclosure, a method for treating tissue is provided including ultrasonically treating tissue by oscillating a blade of an ultrasonic surgical instrument in contact with tissue and activating a fluid control system to pump the cooling fluid through a blade conduit to cool the blade. The ultrasonic surgical instrument and/or fluid control system may be any of those described herein.

In aspects, activating the fluid control system includes depressing an activation button to activate the fluid control system. In aspects, depressing the activation button activates the fluid control system and oscillates the blade. The method may further include releasing the activation button to deactivate the fluid control system and to cease oscillation of the blade. In some aspects, after the activation button is released the method includes delaying the deactivation of the fluid control system until a predetermined amount of time has passed. In particular aspects, the method includes receiving a sensed temperature of the blade after releasing the activation button and deactivating the fluid control system after the sensed temperature of the blade is below a lower temperature limit.

In aspects, the method includes receiving a sensed temperature of the blade and verifying the sensed temperature of the blade is above an upper temperature limit before activating the fluid control system. In aspects, the method includes deactivating the fluid control system after the sensed temperature of the blade is below a lower temperature limit. In some aspects, the method includes inputting the upper temperature limit and/or the lower temperature limit before ultrasonically treating tissue. In particular aspects, the method includes varying the amount of fluid flowing through the blade cooling system in response to the sensed temperature of the blade.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 9 is a perspective view of yet another surgical system provided in accordance with the present disclosure including a surgical instrument incorporating a cooling system;

FIG. 9A is an enlarged view of the detail area "9A" of FIG. 9;

FIG. 10 is a longitudinal, cross-sectional view of the blade of the surgical instrument of FIG. 9 illustrating the cooling system; and FIG. 11 is a longitudinal, cross-sectional view of another blade cooling system provided in accordance with the present disclosure including a cooling conduit disposed within a waveguide.

DETAILED DESCRIPTION

Figure 1:
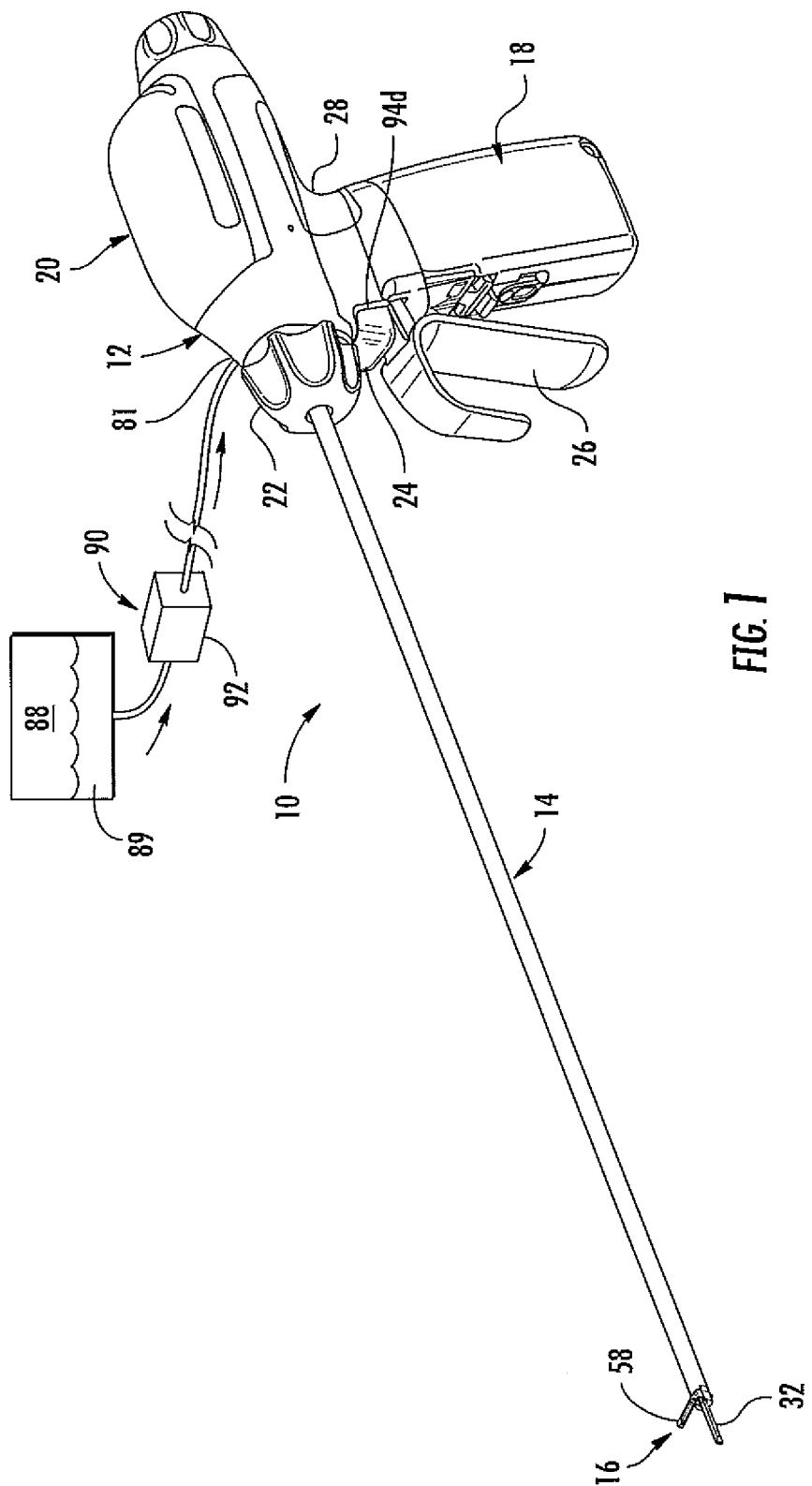
FIG. 1 is a perspective view of a surgical system provided in accordance with the present disclosure including a surgical instrument incorporating a cooling system.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is furthest from the clinician. Throughout the drawings, the arrows within and adjacent to portions of the cooling system indicate the direction of the flow of the cooling fluid.

Referring now to FIG. 1, one exemplary embodiment of an ultrasonic surgical instrument configured for use in accordance with the present disclosure is shown generally identified by reference numeral 10, although it is also envisioned that the aspects and features of the present disclosure be similarly incorporated into any suitable ultrasonic surgical instrument. Ultrasonic surgical instrument 10 generally includes a handle assembly 12, an elongated body portion 14, and a tool assembly 16. Handle assembly 12 supports a battery assembly 18 and an ultrasonic transducer and generator assembly (hereinafter "TAG") 20. Handle assembly 12 includes a rotatable nozzle 22, an activation button 24, and a clamp trigger 26. Battery assembly 18 and TAG 20 are each releasably secured to a central body 28 of handle assembly 12 and are removable from central body 28 to facilitate disposal of the entire device, with the exception of battery assembly 18 and TAG 20.

Figure 2:
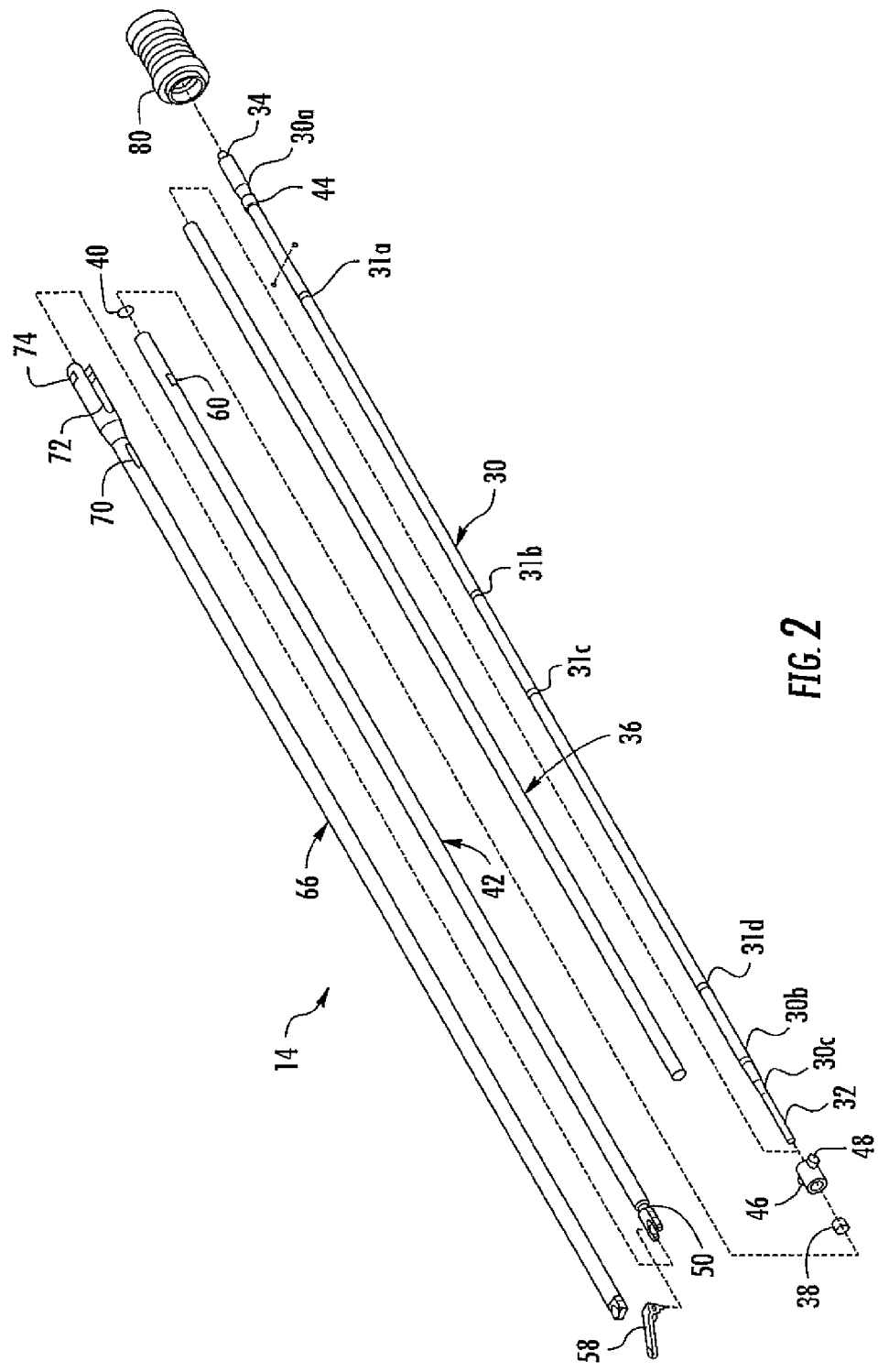
FIG. 2 is an exploded view of the components of the elongated body portion of the surgical instrument of FIG. 1.

With additional reference to FIG. 2, elongated body portion 14 includes a waveguide 30 which extends from handle assembly 12 to tool assembly 16 (FIG. 1). A distal end of waveguide 30 defines a blade 32, which will be discussed in further detail below. A proximal end of waveguide 30 has a threaded extension 34 for engaging TAG 20. Waveguide 30 further includes a proximal tapered portion 30a and distal tapered portions 30b and 30c. A series of annular abutments 31a-d are disposed along, e.g., machined onto, waveguide 30 at node points along waveguide 30.

An inner tube 36 is positioned about waveguide 30 between proximal tapered portion 30a and distal tapered portion 30b of waveguide 30. A distal seal member 38 is supported about waveguide 30 distally of a distal end of inner tube 36 and proximally of distal tapered portion 30c of waveguide 30 to provide a fluid-tight seal at the distal end of elongated body portion 14 between waveguide 30 and an inner surface of a middle tube 42. Ultrasonic energy is isolated from transfer to middle tube 42 by inner tube 36. A series of splines 44 are formed at the proximal end of waveguide 30. Splines 44 engage splines (not shown) formed on an inner surface of a torque adapter 46 to rotatably secure torque adapter 46 to waveguide 30. Torque adapter 46 also includes diametrically opposed wings 48 which are positioned in recesses (not shown) in rotatable nozzle 22 to secure torque adapter 46 to rotatable nozzle 22.

Figure 3:
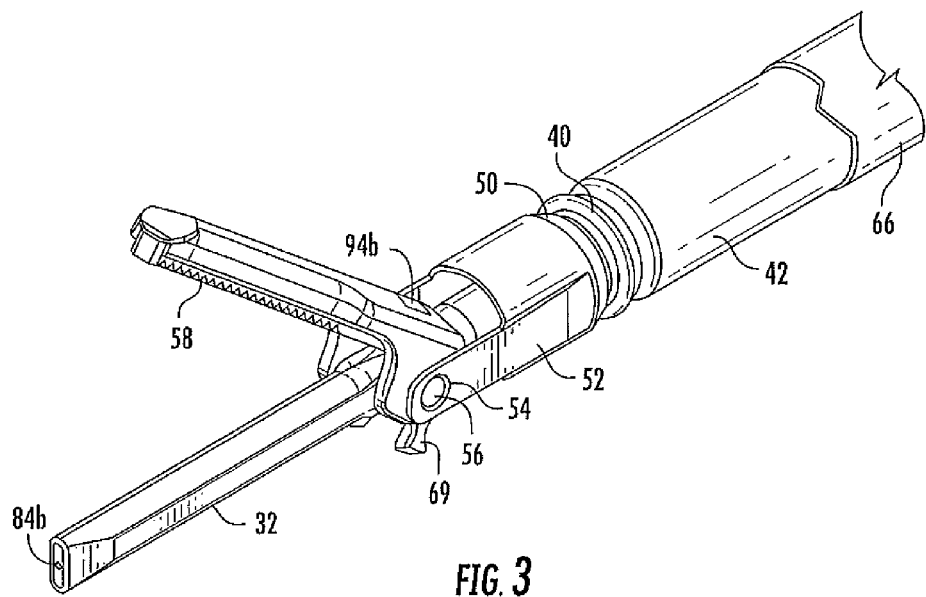
FIG. 3 is an enlarged view of the tool assembly of the surgical instrument of FIG. 1 with a portion of the outer tube of the surgical instrument cut away.
Figure 3A:
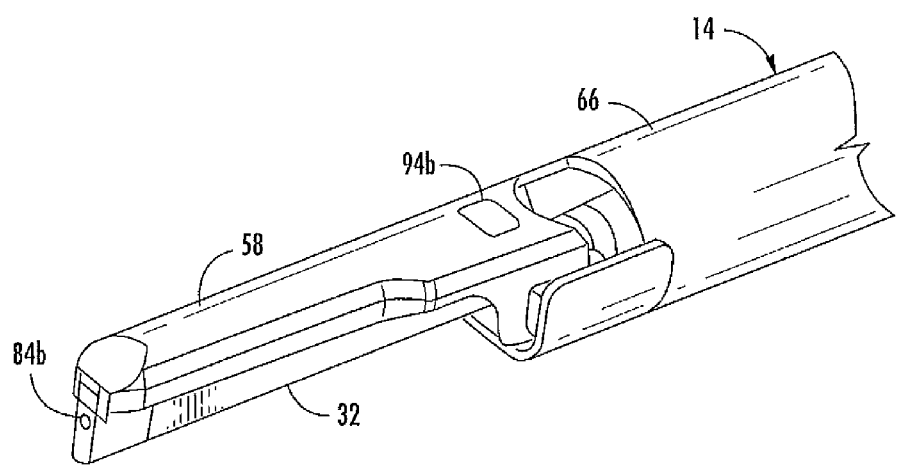
FIG. 3A is an enlargement of the distal end of the surgical instrument of FIG. 1 with the tool assembly in the closed position.

With additional reference to FIGS. 3 and 3A, middle tube 42 is positioned about inner tube 36 and includes a distal end having a corset feature 50 and a pair of spaced clamp support arms 52. Corset feature 50 is positioned to receive distal seal member 38 to maintain distal seal member 38 in the proper position about the distal end of waveguide 30. Distal seal member 38 is positioned at a node point along waveguide 30. An O-ring 40 is supported about corset feature 50 to provide a fluid-tight seal between an outer surface of middle tube 42 and an inner surface of an outer tube 66.

With particular reference to FIGS. 3 and 3A, spaced clamp support arms 52 each define an opening 54 for pivotally receiving pivot members 56 formed on a clamp member 58 of tool assembly 16. Clamp member 58 of tool assembly 16 is pivotal between an open position (FIG. 3), wherein clamp member 58 is spaced from blade member 32, and a closed position (FIG. 3A), wherein clamp member 58 is in juxtaposed alignment with blade member 32. Clamp member 58 is moved between the open position and the closed position in response to actuation of clamp trigger 26 (FIG. 1).

Outer tube 66 is slidably repositionable between an advanced position and a retracted position. Upon movement of outer tube 66 from the advanced position to the retracted position, clamp member 58 is moved from the open position (FIG. 3) to the closed position (FIG. 3A). A proximal end of outer tube 66 includes an elongated slot 70 (FIG. 2) which receives projections (not shown) of rotatable nozzle 22 (FIG. 1) such that outer tube 66 is rotatably secured to, but slidable about, the projections to facilitate movement of outer tube 66 between the advanced and retracted positions.

Referring again to FIG. 2, the proximal end of outer tube 66 includes a bifurcated portion that defines an axially extending throughbore 72 that slidably receives wings 48 of torque adapter 46. A pair of diametrically opposed windows 74 are formed in the proximal end of outer tube 66. Windows 74 receive bosses (not shown) formed in handle assembly 12 (FIG. 1) to couple outer tube 66 to handle assembly 12 (FIG. 1).

Figure 4:
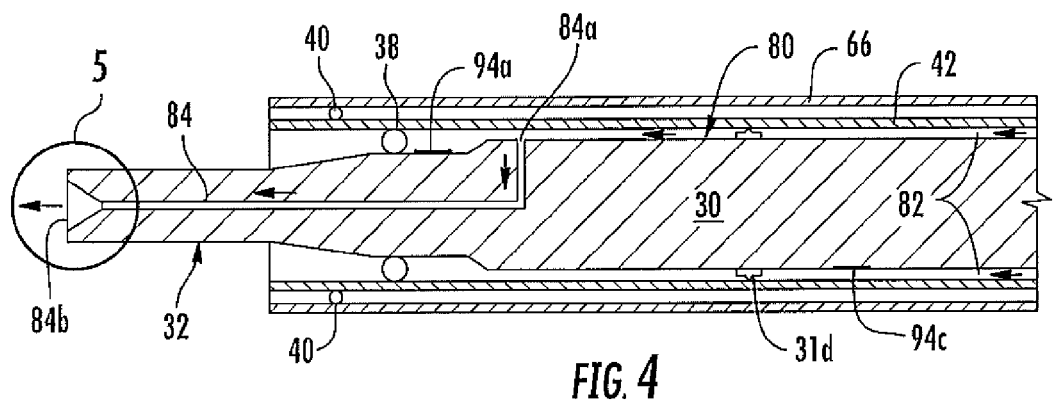
FIG. 4 is a longitudinal, cross-sectional view of the distal end of the surgical instrument of FIG. 1 illustrating operation of the cooling system.
Figure 5:
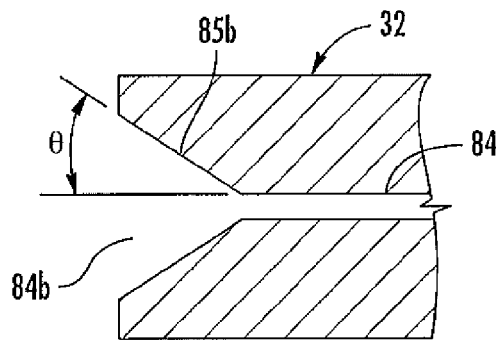
FIG. 5 is an enlarged view of the detail area "5" of FIG. 4.

Referring to FIG. 4, one embodiment of a blade cooling system 80 incorporated into ultrasonic surgical instrument 10 (FIG. 1) in accordance with the present disclosure is shown including an inflow conduit 82 and a blade conduit 84. Inflow conduit 82 is annularly defined between middle tube 42 and waveguide 30. Blade conduit 84 is formed within and extends substantially through the length of blade 32. Blade conduit 84 includes one or more blade inlets 84a, e.g., one or more blade inlets 84a extending radially outwardly from blade conduit 84, and a blade outlet 84b. Blade inlet(s) 84a may be positioned at an anti-node point along waveguide 30. Blade outlet 84b is defined at the distal end of blade 32. Blade conduit 84 is in fluid communication with inflow conduit 82 via blade inlet(s) 84a. Blade outlet 84b includes an angled surface 85b disposed at an angle θ to the inner surface of blade conduit 84 as shown in FIG. 5 to facilitate the outflow of fluid from blade conduit 84. Angle θ may be in a range of about 0° to about 45°. Blade conduit 84 may have a diameter in the range of about 0.25 mm to about 0.65 mm. In embodiments, blade inlet 84a may have a diameter in the range of about 0.25 mm to about 1.00 mm. Other suitable configurations are also contemplated.

As noted above, inflow conduit 82 is defined between middle tube 42 and waveguide 30. Alternatively or additionally, inflow conduit 82 may be defined between outer tube 66 and middle tube 42. In such embodiments, inflow conduit 82 includes an input opening (not shown) in inner tube 36 and/or middle tube 42, which provides fluid communication between inflow conduit 82 and blade inlet 84a.

Annular abutment 31d is positioned within inflow conduit 82 and configured to permit a cooling fluid 89 (FIG. 1) to flow through inflow conduit 82 to blade inlet 84a. In embodiments, as opposed to defining inflow conduit 82 annularly between middle tube 42 and waveguide 30, inflow conduit 82 may comprise one or more polyimide microtubes (or other suitable microtubes) disposed between inner tube 36 and waveguide 30 and extending proximally from the proximal end of elongated body member 14. In such configurations, annular abutment 31d may include a passage (or passages) dimensioned and configured to slidably receive the one or more microtubes.

Referring to FIGS. 1-4, blade cooling system 80 further includes a fluid reservoir 88 in fluid communication with inflow conduit 82. Fluid reservoir 88 may be positioned external to instrument 10, positioned on handle assembly 12, or positioned within handle assembly 12. In embodiments where fluid reservoir 88 is external to instrument 10, central body 28 of handle assembly 12 includes an inflow port 81 to provide fluid communication between fluid reservoir 88 and inflow conduit 82. Fluid reservoir 88 is configured to hold a supply of cooling fluid 89. Cooling fluid 89 can be any fluid capable of conductively and/or conventionally absorbing heat from a thermally conductive solid surface. Exemplary cooling fluids include but are not limited to water, saline, compressed air, compressed nitrogen, compressed oxygen, etc.

Blade cooling system 80 further includes a fluid control system 90 having a pump 92. Pump 92 is configured to pump cooling fluid 89 from fluid reservoir 88 through inflow conduit 82 and blade conduit 84 such that cooling fluid 89 exits blade 32 through blade outlet 84b. In embodiments, fluid control system 90 is selectively operated by a clinician. In some embodiments, fluid control system 90 is automatically operated by conditions of instrument 10 sensed by fluid control system 90. Fluid control system 90 may include a plurality of sensors 94a-d positioned on and/or within instrument 10 to provide feedback of conditions of instrument 10. Sensors 94a-d may include, for example, a blade thermocouple 94a configured to measure the temperature of blade 32, a clamp sensor 94b (FIG. 3) configured to determine the position of clamp 58 and/or the position of clamp trigger 26, a waveguide thermocouple 94c configured to measure the temperature of a portion of waveguide 14, and an activation sensor 94d configured to measure the position of activation button 24. Other suitable sensors and/or combinations of sensors are also contemplated, as are any other suitable mechanisms for providing feedback and/or indicating a state, parameter, condition, etc. of a component of instrument 10 and/or the surrounding environment.

When pump 92 of fluid control system 90 is activated, pump 92 draws cooling fluid 89 from fluid reservoir 88 and pumps cooling fluid 89 through inflow conduit 82 and blade conduit 84. When cooling fluid 89 is pumped through blade conduit 84, cooling fluid 89 flows out of blade outlet 84b formed through the distal surface of blade 32 (see FIGS. 3-3A). As cooling fluid 89 exits from blade outlet 84b, cooling fluid 89 can form a mist. As angle θ of angled surface 85b is decreased, the misting of cooling fluid 89 decreases. As cooling fluid 89 fluid flows through blade conduit 84, cooling fluid 89 absorbs heat from blade 32 such that blade 32 is cooled by blade cooling system 80. Cooling fluid 89 flowing through inflow conduit 82 also absorbs heat from waveguide 30. Fluid control system 90 regulates the amount of cooling fluid 89 that pump 92 draws from fluid reservoir 88 and pumps through blade cooling system 80 thus controlling the cooling of blade 32.

Fluid control system 90 may be configured to control the cooling of blade 32 via regulating pump 92 such as, for example, by: activating pump 92 to continually pump cooling fluid 89 through blade cooling system 80; activating/deactivating pump 92 to pump cooling fluid 89 through blade cooling system 80 when activation button 24 (FIG. 1) is depressed (actuated); activating/deactivating pump 92 to pump cooling fluid 89 through blade cooling system 80 when activation button 24 (FIG. 1) is released (un-actuated); activating/deactivating pump 92 to pump cooling fluid 89 through blade cooling system 80 according to a predetermined schedule; activating/deactivating pump 92 to pump cooling fluid 89 through blade cooling system 80 once activation button 24 (FIG. 1) has been depressed (actuated) for a predetermined period of time; activating/deactivating pump 92 to pump cooling fluid 89 through blade cooling system 80 once activation button 24 (FIG. 1) has been released (un-actuated) for a predetermined amount of time; and/or activating/deactivating pump 92 to pump cooling fluid 89 through blade cooling system 80 based upon temperature feedback so as to maintain the temperature of blade 32 and/or waveguide 30 below a predetermined threshold temperature or within a predetermined temperature range. As described in detail below, fluid control system 90 may include sensors 94a-d, or any other suitable mechanisms for providing feedback and/or indicating a state, parameter, condition, etc. of a component of instrument 10 and/or the surrounding environment, to facilitate controlling of pump 92. Other control systems, mechanisms, methods, and/or protocols are also contemplated.

As mentioned above, in some embodiments, fluid control system 90, together with blade cooling system 80, may be configured to maintain blade 32 below a predetermined temperature. In such a configuration, the clinician inputs an upper temperature limit into fluid control system 90. In embodiments, the upper temperature limit may also be preset at the time of manufacture of fluid control system 90. Fluid control system 90 activates pump 92 when blade thermocouple 94a determines the temperature of blade 32 is approaching the upper temperature limit. When pump 92 is activated, pump 92 pumps cooling fluid 89 through blade cooling system 80 to prevent blade 32 from exceeding the upper temperature limit. The amount of fluid pumped through blade cooling system 80 may also be varied depending on the sensed temperature.

Additionally, blade 32 may be maintained within a range of predetermined temperatures. In such a configuration, the clinician inputs an upper and lower temperature limit of the range of predetermined temperatures into fluid control system 90. Similar to the previous configuration, the upper and lower temperature limits can be preset. Fluid control system 90 activates pump 92 (or increases the rate at which fluid is pumped) when blade thermocouple 94a determines the temperature of blade 32 is approaching the upper temperature limit to cool or decrease the temperature of blade 32. When fluid control system 90 determines the temperature of blade 32 is approaching the lower temperature limit, as measured by blade thermocouple 94c, fluid control system 90 deactivates pump 92 (or decreases the rate at which fluid is pumped) stopping (or reducing) the flow of cooling fluid 89 through blade 32.

Additionally or alternatively, blade cooling system 80 may be configured to cool blade 32 after a clinician has activated and deactivated blade 32. In this configuration blade 32 is allowed to heat up when used to dissect and/or coagulate tissue, but is actively cooled via blade cooling system 10 once blade 32 is no longer in use. In such a configuration, fluid control system 90 activates pump 92 when blade thermocouple 94a determines the temperature of blade 32 exceeds an upper temperature limit and activation sensor 94d (or other suitable mechanism) determines that activation button 24 is in the released (un-actuated) position. Fluid control system 90 may deactivate pump 92 when the temperature of blade 32 reaches a lower temperature limit, or when activation button 24 is in the depressed (actuated) position. Fluid control system 90 may further include a clamp sensor 94b (or other suitable mechanism) to determine the position of clamp 58, i.e. open or closed. When clamp 58 is in the open position, as determined by clamp sensor 94b, and the temperature of blade 32 exceeds the upper temperature limit, fluid control system 90 activates pump 92. On the other hand, when clamp 58 or the temperature of blade 32 is below the lower temperature limit, fluid control system 90 deactivates pump 92.

Figure 6:
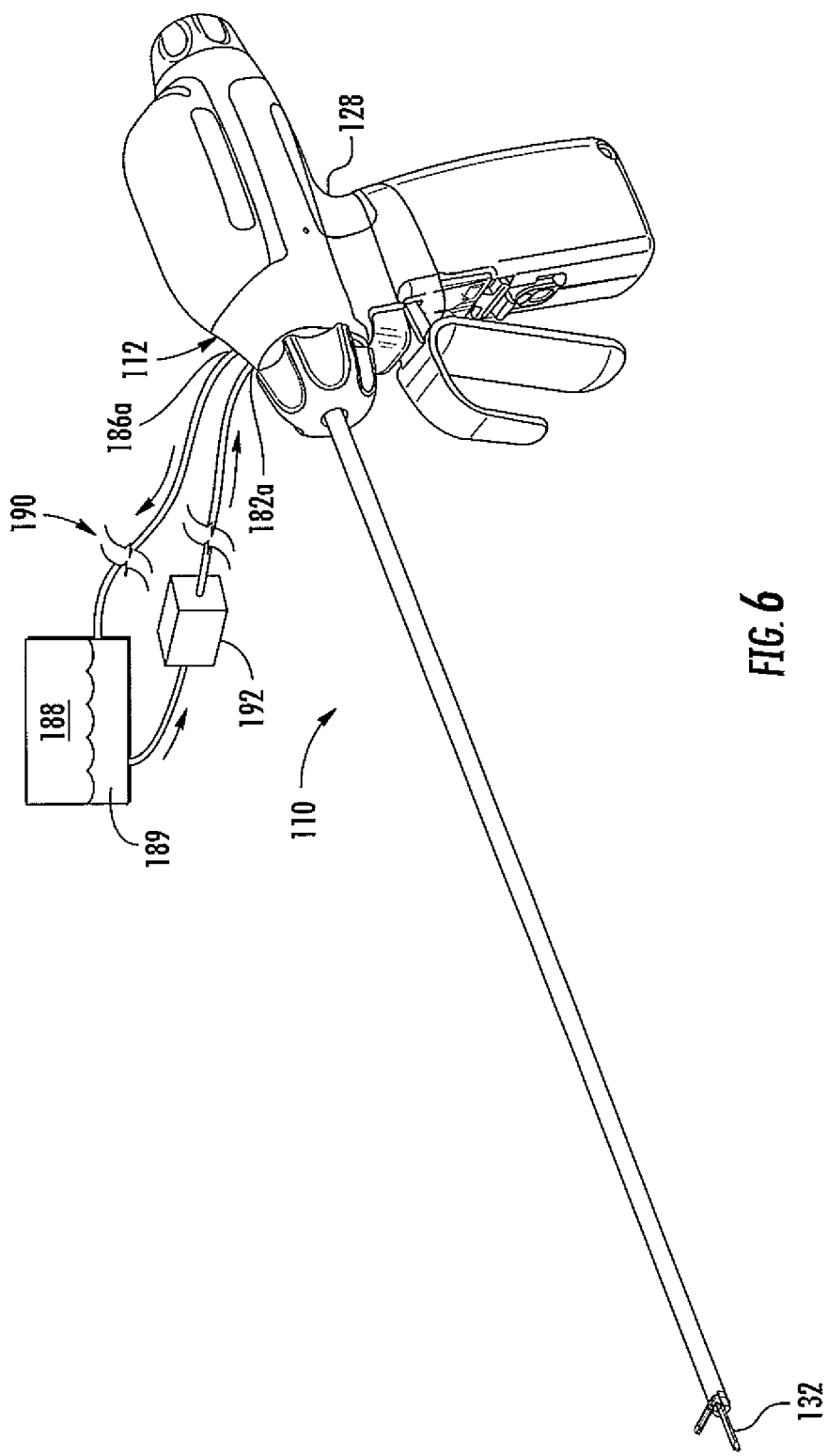
FIG. 6 is a perspective view of another surgical system provided in accordance with the present disclosure including a surgical instrument incorporating a cooling system.
Figure 7:
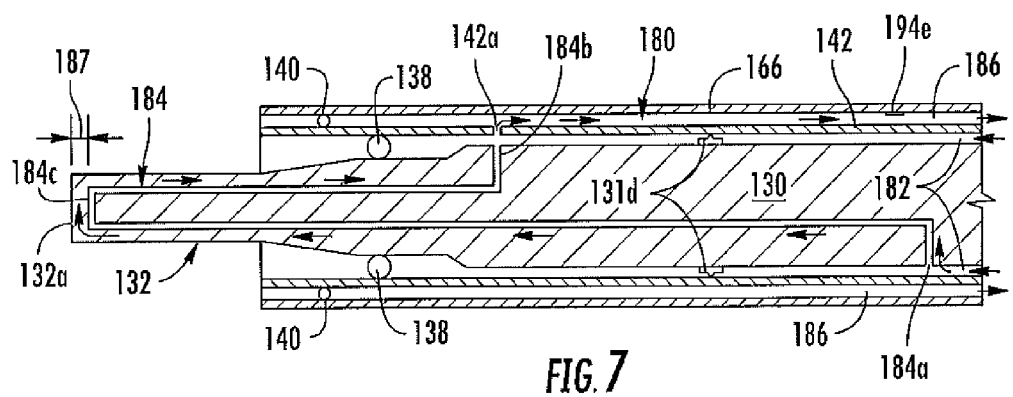
FIG. 7 is a longitudinal, cross-sectional view of the distal end of the surgical instrument of FIG. 6 illustrating operation of the cooling system.

Referring to FIGS. 6 and 7, another ultrasonic surgical instrument 110 is provided in accordance with the present disclosure including a waveguide 130 and incorporating a blade cooling system 180. Ultrasonic instrument 110 and blade cooling system 180 are substantially similar to ultrasonic instrument 10 and blade cooling system 80 (FIGS. 1-5), with similar elements represented by similar numerals. As such only the differences are discussed in detail below.

Blade cooling system 180 is a closed circuit and includes an inflow conduit 182, a blade conduit 184, and a return conduit 186. Inflow conduit 182 is defined between middle tube 142 and waveguide 130. Inflow conduit 182 is in fluid communication with blade conduit 184 via one or more blade inlets 184a disposed at an anti-node point along waveguide 130. A seal is disposed about or in proximity to annular abutment 131d to seal a distal end of inflow conduit 182. In embodiments, annular abutment 131d forms a seal at the distal end of inflow conduit 182. Blade conduit 184 is defined within and extends through blade 132. Blade conduit 184 includes blade inlet(s) 184a and a blade outlet 184b. Blade inlet(s) 184a is proximal of the seal of, about, or in proximity to annular abutment 131d to permit the inflow of fluid from inflow conduit 182 into blade inlets) 184a. Blade conduit 184 extends distally from blade inlet 184a such that blade conduit 184 extends substantially along the length of blade 132 in a parallel orientation to the longitudinal axis. A distal section 184c of blade conduit 184 is orthogonal to the longitudinal axis of blade 132 (or otherwise curved, bent, or angled) such that distal section 184*c* of blade conduit 184 is parallel (or otherwise curved, bent, or angled) to a distal surface 132*a* of blade 132. Distal section 184*c* is spaced-apart from distal surface 132*a* of blade 132 and distal section 184*c* defining a gap 187 therebetween. Gap 187 may be in the range of about 0.005 to about 0.025 mm; however, larger and smaller dimensions for gap 187 are also contemplated. Blade conduit 184 returns along a length of blade 132 from distal section 184*c* to blade outlet 184*b*. Blade outlet 184*b* disposed at an anti-node point along waveguide 130 and is disposed in fluid connection with return conduit 186, e.g., via positioning of blade outlet 184*b* proximally of distal seal member 138 and distally of the seal of, about, or in proximity of annular abutment 131*d*. Return conduit 186 is defined between middle tube 142 and outer tube 166 and is in fluid communication with blade outlet 184*b* through a slot 142*a* of middle tube 142. An O-Ring 140 is positioned distal to slot 142*a* between middle tube 142 and outer tube 166 to seal the distal end of return conduit 186.

Figure 8:
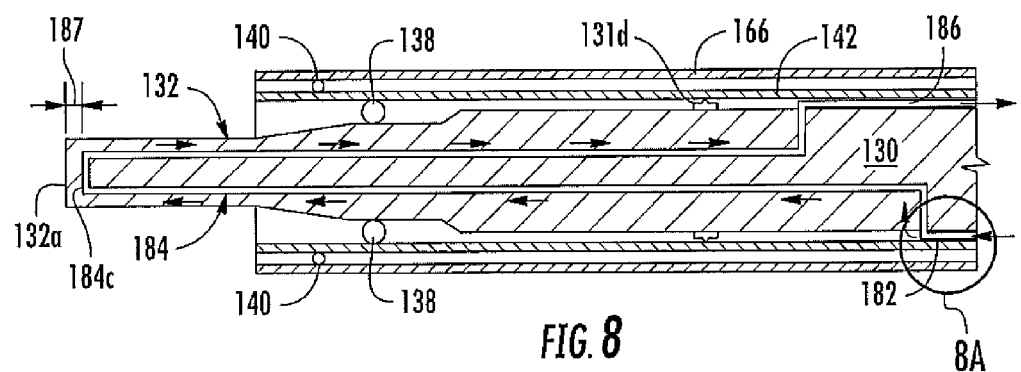
FIG. 8 is a longitudinal, cross-sectional view of another cooling system provided in accordance with the present disclosure and configured for use with the surgical instrument of FIG. 6.
Figure 8A:
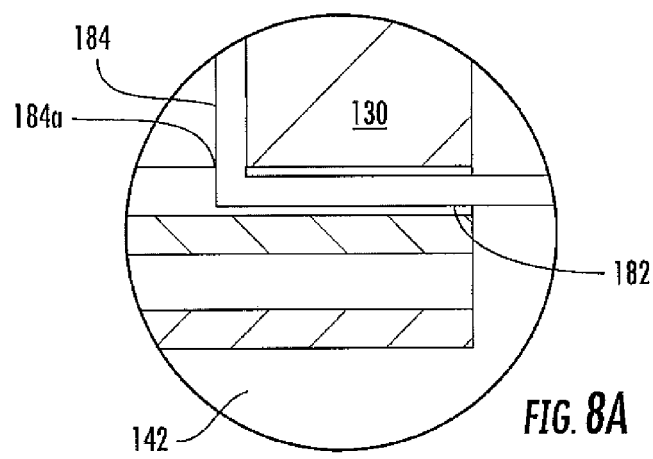
FIG. 8A is an enlarged view of the detail area "8A" of FIG. 8.

Similar to inflow conduit 82 described above (FIG. 4), inflow conduit 182 and return conduit 186 may alternatively be formed from polyimide microtubes. For example, inflow conduit 182 can be a polyimide microtube disposed between middle tube 142 and waveguide 130 and in fluid communication with blade inlet 184*a* and return conduit 186 can be a polyimide microtube in fluid communication with blade outlet 184*b* passing through slot 142*a* of middle tube 142 and extending proximally through a channel disposed between outer tube 166 and middle tube 142. Moreover, as shown in FIGS. 8 and 8A, in embodiments where microtubes are provided, conduits 182, 186 of polyimide microtubes may be disposed within the same channel, e.g., between the middle tube 142 and the waveguide 130, and blade outlet 184*b* can be proximal to annular abutment 31*d*.

In embodiments, return conduit 186 is in fluid communication with inflow conduit 182 such that the fluid continually circulates through blade cooling system 180. In some embodiments, blade cooling system 180 includes a fluid control system 190 having a pump 192 positioned between return conduit 186 and inflow conduit 182 to circulate cooling fluid 189 through blade cooling system 180. Pump 192 can be disposed within central body 128 of handle assembly 112. In certain embodiments, blade cooling system 180 further includes a fluid reservoir 188 positioned between and in fluid communication with return conduit 186 and inflow conduit 182. Fluid reservoir 188 can be disposed within central body 128 or external to instrument 110. When fluid reservoir 188 is disposed external to instrument 110, central body 128 includes an inflow port 182*a* and a return port 186*a* in fluid communication with inflow conduit 182 and return conduit 186, respectively. Fluid control system 190 may also include a sensors 194*a-d* similar to the sensors 94*a-d* discussed above with respect to instrument 10 (FIGS. 1-5) and may also include a return conduit thermocouple 194*e* (FIG. 7) configured to measure the temperature of cooling fluid 189 in return conduit 186.

Blade cooling system 180 of instrument 110 functions substantially similar to blade cooling system 80 of instrument 10. However, as blade cooling system 180 is a closed system, cooling fluid 189 flows through inflow conduit 182 through blade conduit 184 and returns through return conduit 186 before recirculating through blade cooling system 180. As cooling fluid 189 flows through blade cooling system 180, cooling fluid 189 absorbs heat from waveguide 130 and/or blade 132. The absorbed heat may be released to the surrounding environment through an outer surface of outer tube 166, central portion 128 of housing assembly 112, and/or from fluid reservoir 188. Additionally, fluid reservoir 188 may be actively cooled to facilitate cooling of the fluid 189 returned from blade 132 prior to recirculation.

Referring to FIGS. 9-10, another ultrasonic instrument 210 is provided in accordance with the present disclosure including a waveguide 230 and incorporating a blade cooling system 280. Ultrasonic instrument 210 and blade cooling system 280 are substantially similar to ultrasonic instrument 10 and blade cooling system 80 (FIGS. 1-5), with similar elements represented by similar numerals. As such only the differences are discussed in detail below.

Blade cooling system 280 includes a blade conduit 284 and a cooling conduit 286. It is envisioned that the distal end 284*a* of blade conduit 284 is spaced from a distal surface 232*a* of blade 232 by a gap 287. Gap 287 may be in the range of about 0.005 to about 0.025 mm; however, larger and smaller dimensions for gap 287 are also contemplated. Blade conduit 284 extends proximally within and substantially along the length of blade 232 to a blade outlet 284*b*. Cooling conduit 286 is disposed within blade conduit 284 and a longitudinal slot 266*a* in the outer surface of outer tube 266 along a length of an elongated body portion 214 (see FIG. 9A). A proximal end 286*b* of cooling conduit 286 may be sealed or may be configured to couple to a fluid reservoir similarly as described above with respect to previous embodiments. A distal end 286*a* of cooling conduit 286 is proximate to distal end 284*a* of blade conduit 284. Cooling conduit 286 can be a polyimide tube.

Referring to FIG. 11, a blade cooling system 380 is provided in accordance with the present disclosure incorporated within a waveguide 330 and blade 332. Waveguide 330 and blade cooling system 380 are substantially similar to waveguide 30 and blade cooling system 80 (FIGS. 1-5), with similar elements represented by similar numerals, and may be used with any of ultrasonic instruments 10, 110, and 210. It is also contemplated that blade cooling system 380 can be used with other suitable ultrasonic instruments. As such only the differences are discussed in detail below.

Blade cooling system 380 is a closed heat pipe system and includes a blade conduit 384 and a cooling conduit 386. It is envisioned that the distal end 384*a* of blade conduit 384 is spaced from a distal surface 332*a* of blade 332 by a gap 387. Gap 387 may be in the range of about 0.005 to about 0.025 mm; however, larger and smaller dimensions for gap 387 are also contemplated. Blade conduit 384 extends proximally within and substantially along the length of blade 332 to a blade outlet 384*b*. Blade outlet 384*b* is in fluid communication with cooling conduit 386, i.e., blade conduit 384 and cooling conduit 386 cooperate to define a heat pipe extending through and between at least a portion of both waveguide 330 and blade 332. Cooling conduit 386 is disposed within waveguide 330. Cooling conduit 386 includes a conduit opening 386*a* at a distal end of waveguide 330 in fluid communication with blade outlet 384*b* and a proximal or closed end 386*b* is proximate to the proximal end of waveguide 330. Closed end 386*b* of cooling conduit 386 is sealed. In embodiments, the inner wall of the blade conduit 384 and/or cooling conduit 386 includes a wick structure (not shown) configured to exert capillary pressure on the cooling fluid when the cooling fluid is in a liquid phase. The wick structure may be a series of grooves parallel to the longitudinal axis of waveguide 330. Cooling conduit 386 is constructed of a material with a high thermal efficiency, e.g., copper, polyimide micro tubing, etc.

In use, as the temperature of blade 332 increases, cooling fluid 389 which is disposed within blade conduit 384 absorbs heat from blade 332 transitioning cooling fluid 389 from a liquid phase to a vapor phase. Cooling fluid 389 in the vapor phase travels through blade cooling system 380 from blade conduit 384 to cooling conduit 386 where the cooling fluid 389 releases the absorbed heat through the surface of cooling conduit 386, i.e., waveguide 330, to the surrounding environment. As cooling fluid 389 releases the absorbed heat, cooling fluid 389 returns from the vapor phase to the liquid phase. When cooling fluid 389 returns to the liquid phase, cooling fluid 389 returns to blade conduit 384 to repeat the cycle. As can be appreciated, the distal-to-proximal movement of the vapor and the proximal-to-distal movement of the liquid can be facilitated by gravity when in use as blade 332 is generally angled downwardly relative to waveguide 330 into the surgical site.

The present disclosure also provides methods of manufacturing ultrasonic surgical instruments including cooling systems, such as those instruments detailed above. The method may include fabricating a waveguide, fabricating two halves of a blade separated along the longitudinal axis of the blade, cutting a portion of a conduit in each half of the blade, welding the two halves of the blade into a blade, and welding the blade to the distal end of the waveguide. As such, the conduits extending through the blade, as detailed above, can be readily formed to a desired configuration.

Cutting a portion of the conduit in each half of the blade may particularly include cutting a half-cylindrical channel along the length of the blade half including an opening in the outer surface of the blade and at the distal end of the blade. Blade 32 (FIG. 4) may be manufactured in this manner. Alternatively, to achieve blade 132 (FIG. 7), the cutting a portion of the conduit in each half of the blade includes cutting a half-cylindrical channel along the length of the blade half from a first opening in the outer surface of the blade, along the length of the blade towards the distal end, continuing the channel substantially parallel to the distal end of the blade defining a gap between the channel and the distal end of the blade, continuing the channel back along the length of the blade towards the proximal end of the blade, continuing the channel out a second opening in the outer surface of the blade substantially opposing the first opening. The cutting in either of the above embodiments may be accomplished by laser cutting or etching.

Welding the two halves of the blade into a blade may include aligning the two halves of the blade such that the half-cylindrical channels in each blade are positioned adjacent to each other to form a continuous cylindrical conduit within the blade. Welding the two halves may include laser welding the two halves of the blade together. Welding the blade to the waveguide may include laser welding the proximal end of the blade to the distal end of the waveguide.

In embodiments, the distal end of the waveguide includes threads configured to cooperate with threads of the blade to secure the waveguide to the blade. In some embodiments, Electrical Discharge Machining (EDM) is used to make the blade conduit, and then the distal end of the blade is welded shut. Other suitable manufacturing methods are also contemplated.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed:

1. A method of treating tissue, comprising:
   depressing an activation button of the ultrasonic surgical instrument to ultrasonically treat tissue by oscillating a blade of an ultrasonic surgical instrument in contact with tissue, the blade defining a blade conduit extending at least partially therethrough, wherein depressing the activation button also activates a fluid control system to pump cooling fluid through an inflow conduit and into an inlet of the blade conduit to cool the blade, the inflow conduit defined about a waveguide that supports the blade at a distal end thereof;
   releasing the activation button to deactivate the fluid control system and to cease oscillation of the blade; and
   receiving a sensed temperature of the blade after releasing the activation button, wherein deactivating the fluid control system includes deactivating the fluid control system once the sensed temperature of the blade is below a lower temperature limit.

2. The method of claim 1, wherein deactivation of the fluid control system is delayed a predetermined amount of time after release of the activation button.

3. A method of treating tissue, comprising:
   ultrasonically treating tissue by oscillating a blade of an ultrasonic surgical instrument in contact with tissue, the blade defining a blade conduit extending at least partially therethrough;
   activating a fluid control system to pump cooling fluid through an inflow conduit and into an inlet of the blade conduit to cool the blade; and
   receiving a sensed temperature of the blade and activating the fluid control system once the sensed temperature of the blade is above an upper temperature limit.

4. The method of claim 3 further including deactivating the fluid control system after the sensed temperature of the blade is below a lower temperature limit.

5. The method of claim 3 further including inputting the upper temperature limit before ultrasonically treating tissue.

6. The method of claim 4 further including inputting the lower temperature limit before ultrasonically treating tissue.

7. A method of treating tissue, comprising:
   ultrasonically treating tissue by oscillating a blade of an ultrasonic surgical instrument in contact with tissue, the blade defining a blade conduit extending at least partially therethrough;
   activating a fluid control system to pump cooling fluid through an inflow conduit and into an inlet of the blade conduit to cool the blade; and
   receiving a sensed temperature of the blade and varying the amount of fluid flowing through the blade cooling system in response to the sensed temperature of the blade.

\* \* \* \* \*